United States Patent
Kim et al.

(10) Patent No.: US 10,099,213 B2
(45) Date of Patent: Oct. 16, 2018

(54) PROCESSES FOR REGENERATING CATALYSTS USEFUL IN FISCHER-TROPSCH PROCESSES

(71) Applicant: CLARIANT CORPORATION, Louisville, KY (US)

(72) Inventors: Jae Hyung Kim, Louisville, KY (US); Doug Huelsman, Louisville, KY (US); Jeffery L. Braden, New Albany, IN (US)

(73) Assignee: Clariant Corporation, Louisville, KY (US)

(*) Notice: Subject to any disclaimer, the term of this patent is extended or adjusted under 35 U.S.C. 154(b) by 0 days.

(21) Appl. No.: 15/352,736

(22) Filed: Nov. 16, 2016

(65) Prior Publication Data
US 2017/0144144 A1    May 25, 2017

Related U.S. Application Data

(60) Provisional application No. 62/258,729, filed on Nov. 23, 2015.

(51) Int. Cl.

| | |
|---|---|
| *B01J 38/00* | (2006.01) |
| *B01J 38/12* | (2006.01) |
| *B01J 23/75* | (2006.01) |
| *B01J 38/04* | (2006.01) |
| *B01J 38/10* | (2006.01) |
| *C10G 2/00* | (2006.01) |
| *B01J 38/56* | (2006.01) |
| *C07C 1/04* | (2006.01) |

(52) U.S. Cl.
CPC .............. *B01J 38/12* (2013.01); *B01J 23/75* (2013.01); *B01J 38/04* (2013.01); *B01J 38/10* (2013.01); *B01J 38/56* (2013.01); *C07C 1/045* (2013.01); *C10G 2/33* (2013.01); *C10G 2300/70* (2013.01)

(58) Field of Classification Search
CPC ... C10G 2/32; B01J 38/02; B01J 38/04; B01J 38/10; B01J 38/12–38/40
USPC .................................. 502/34, 38–53
See application file for complete search history.

(56) References Cited

U.S. PATENT DOCUMENTS

| | | | | |
|---|---|---|---|---|
| 2,259,961 | A * | 10/1941 | Myddleton | B01J 38/00 502/22 |
| 2,540,109 | A * | 2/1951 | Friedman | B01J 23/94 502/34 |
| 6,201,030 | B1 * | 3/2001 | Beer | B01J 23/94 518/706 |
| 6,787,496 | B2 | 9/2004 | Daage | |
| 6,838,487 | B1 | 1/2005 | Demirel | |
| 6,878,655 | B2 | 4/2005 | Raje | |
| 6,914,082 | B2 | 7/2005 | Zhang | |
| 6,989,403 | B2 | 1/2006 | Huang | |
| 7,179,766 | B2 | 2/2007 | Wolfe | |
| 8,314,043 | B2 | 11/2012 | Lansink Rotgerink | |
| 8,809,215 | B2 | 8/2014 | Van de Loosdrecht | |
| 8,921,252 | B2 | 12/2014 | Rytter | |
| 2003/0166451 | A1 * | 9/2003 | Koveal | B01J 23/94 502/38 |

FOREIGN PATENT DOCUMENTS

WO      02/085508    * 10/2002

* cited by examiner

*Primary Examiner* — Steven J Bos

(57) ABSTRACT

The present disclosure relates to processes for regenerating catalysts. In certain aspects, a process for regenerating a deactivated catalyst disposed in a first organic material includes removing a substantial portion of the first organic material from the catalyst to provide a dewaxed catalyst having less than about 40 wt % (e.g., less than about 20%) organic material disposed thereon. The dewaxed catalyst is then contacted with a flow of a substantially inert gas at a temperature of at least about 200° C. to provide an inert gas-treated catalyst having less than about 10 wt % organic material disposed thereon. The inert gas-treated catalyst is then contacted with an oxygen-containing gas at a temperature of at least about 200 ° C. to form an oxidized catalyst (e.g., having less than 2 wt % carbonaceous material disposed thereon). The oxidized catalyst is then contacted with a hydrogen-containing gas at a temperature of at least about 200° C. to form a regenerated catalyst. Finally, the regenerated catalyst can be disposed in a second organic material. The regenerated catalysts can be useful, for example, in Fischer-Tropsch processes.

18 Claims, 2 Drawing Sheets

PROCESSES FOR REGENERATING CATALYSTS USEFUL IN FISCHER-TROPSCH PROCESSES

BACKGROUND OF THE DISCLOSURE

1. Field of the Disclosure

The present disclosure relates generally to catalysts and processes involving them. The present disclosure relates more particularly to processes for regenerating catalysts for use in Fischer-Tropsch processes.

2. Technical Background

The Fischer-Tropsch process can be used for the conversion of synthesis gas ("syngas," a mixture of $H_2$ and CO) into liquid and/or solid hydrocarbons. The syngas can be made from a variety of feedstocks (e.g. natural gas, associated gas and/or coal-bed methane, biomass, residual oil fractions and coal). Fischer-Tropsch processes are conducted in a reactor in the presence of a suitable catalyst at elevated temperature and pressure to form paraffinic compounds ranging from methane to high molecular weight compounds comprising up to 200 carbon atoms, or, under particular circumstances, even more. Catalyst materials generally include an active component (e.g., a metal, often provided in the form of an oxide) supported on a catalyst support, which can be a porous refractory oxide such as alumina or silica. The support material can provide a high surface area upon which the active component can be dispersed and a pore network through which the reactant gases can diffuse in and the reaction products can diffuse out.

Catalysts become less active over time, thus making the catalyzed process less efficient. Loss of activity can occur via a variety of mechanisms. For example, the catalyst can be poisoned by a number of different species including, for example, sulfur, sodium, nitrogen or carbon containing compounds, all of which de-activate the catalyst. Accordingly, catalysts are replaced periodically in order to maintain acceptable product yield. However, as a result of the complex procedures and expensive metals (e.g., cobalt) used in catalyst fabrication, replacement of the catalyst can be quite expensive. Thus, it is more desirable to regenerate a catalyst (i.e., returning its activity to a desirable state) instead of replacing it, if possible. There exist methods in the art for regenerating Fischer-Tropsch catalysts; most involve removal of organic materials from the surface of the catalyst and reduction of the catalytic metal (e.g., cobalt) to a substantially metallic state. However, existing processes often do not completely reactivate a deactivated catalyst.

Thus, there remains a need to further improve the methods for regenerating catalysts used in Fischer-Tropsch processes.

SUMMARY OF THE DISCLOSURE

In one aspect, the disclosure provides a process for regenerating a deactivated catalyst, the catalyst being disposed in a first organic material, the catalyst comprising a catalytic metal disposed on a support, the process comprising removing a substantial portion of the first organic material from the catalyst to provide a dewaxed catalyst having less than about 40 wt % organic material disposed thereon;

contacting the dewaxed catalyst with a flow of a substantially inert gas at a temperature of at least about 200° C. to provide an inert gas-treated catalyst having less than about 10 wt % organic material disposed thereon;

contacting the inert gas-treated catalyst with an oxygen-containing gas at a temperature of at least about 200° C., the contacting being performed to substantially remove any residual carbonaceous material remaining disposed on the dewaxed catalyst, thereby forming an oxidized catalyst;

contacting the oxidized catalyst with a hydrogen-containing gas at a temperature of at least about 200° C., the hydrogen-containing gas comprising at least 10 vol % hydrogen, thereby forming a regenerated catalyst; and disposing the regenerated catalyst in a second organic material Another aspect of the disclosure is a regenerated catalyst made by a process as described herein.

Another aspect of the disclosure is a process for forming a hydrocarbon product, comprising contacting a regenerated catalyst made by a process as described herein with carbon monoxide and hydrogen.

DETAILED DESCRIPTION

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the catalyst material). All weight percent values are calculated on an oxide basis.

The inventors have determined that using gas stripping followed by hydrogen treatment may not remove effectively residual organic or carbonaceous residues on the deactivated catalysts. Moreover, processes that remove the organic or carbonaceous residues using oxygen are difficult to control given the exothermicity of the oxidation reaction; such exothermic reactions can even further deactivate the catalyst.

Figure 1:
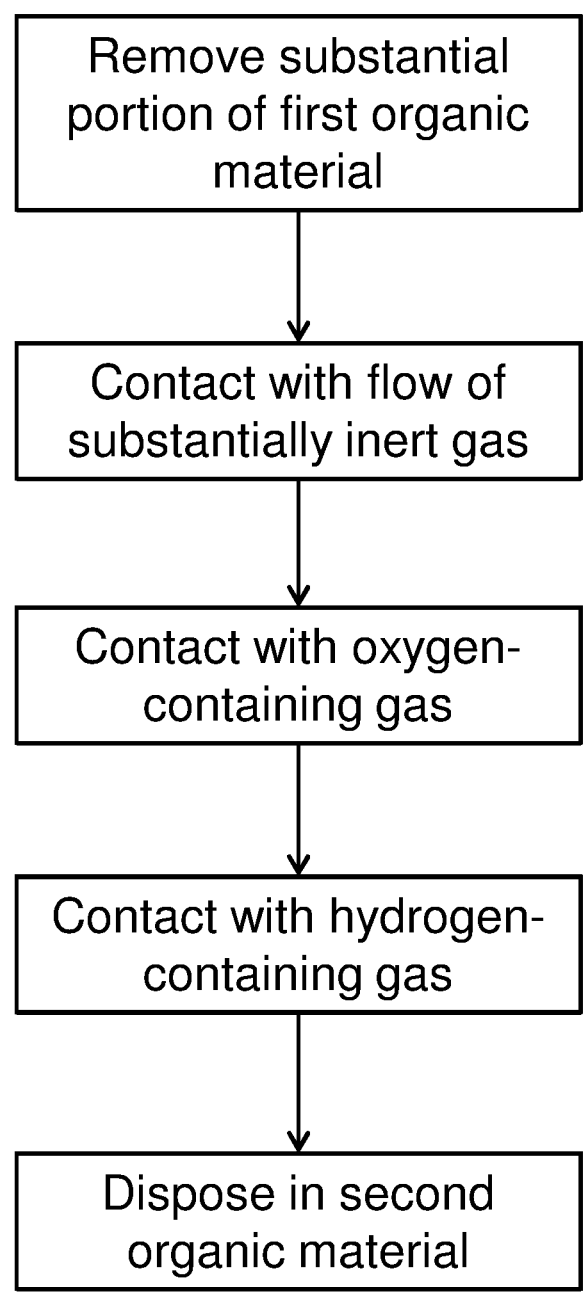
FIG. 1 is a flowchart of a process according to one embodiment of the disclosure.

Accordingly, one embodiment of the disclosure, shown in flowchart view in FIG. 1, is a process for regenerating a deactivated catalyst that is disposed in a first organic material. The catalyst includes a catalytic metal disposed on a support; suitable catalytic metals and support materials are described in more detail below. The process includes removing a substantial portion of the first organic material from the catalyst to provide a dewaxed catalyst having less than about 40 wt % (e.g., less than about 20%) organic material disposed thereon. The dewaxed catalyst is then contacted with a flow of a substantially inert gas at a temperature of at least about 200° C. to provide an inert gas-treated catalyst having less than about 10 wt % organic material disposed thereon. The inert gas-treated catalyst is then contacted with an oxygen-containing gas at a temperature of at least about 200° C. to form an oxidized catalyst. The oxidized catalyst is then contacted with a hydrogen-containing gas at a temperature of at least about 200° C. to form a regenerated catalyst. Finally, the regenerated catalyst can be disposed in a second organic material.

As noted above, the catalyst includes a catalytic metal disposed on a support. The person of ordinary skill in the art will appreciate that a wide variety of catalytic metals and supports can be used. In certain embodiments, the catalytic metal is a Fischer-Tropsch catalytic metal. In certain embodiments, the catalytic metal is selected from among the Group 8 elements of the Periodic Table, such as iron (Fe), ruthenium (Ru), and osmium (Os); Group 9 elements, such as cobalt (Co), rhodium (Rh), and iridium (Ir); Group 10 elements, such as nickel (Ni), palladium (Pd), and platinum (Pt); and the metals molybdenum (Mo), rhenium (Re), and tungsten (W). For example, in one embodiment, the catalytic metal is cobalt, iron, ruthenium, nickel, or a combination thereof. In another embodiment, the catalytic metal is cobalt, iron, ruthenium, or a combination thereof. In certain particular embodiments, the catalytic metal is cobalt. For example, in one embodiment, the catalytic metal is cobalt in combination with one or more of platinum, palladium, gold, ruthenium, rhenium, silver and boron. The catalyst material desirably contains a catalytically effective amount of the catalytic metal(s). As the person of ordinary skill in the art will appreciate, the amount of catalytic metal(s) present in the catalyst may vary widely. The catalyst may further include one or more promoters to modify the catalytic activity of the catalytic metal(s).

The total amount of the catalytic metal(s) and any promoters is desirably in the range of about 1 wt % to about 70 wt % of the total catalyst material on an oxide basis (i.e., as the most stable oxide). In certain embodiments, the total amount of the catalytic metal(s) and any promoters present in the catalyst material is in the range of about 1 wt % to about 60 wt %, or about 1 wt % to about 55 wt %, or about 1 wt % to about 50 wt %, or about 1 wt % to about 40 wt %, or about 1 wt % to about 37 wt %, or about 1 wt % to about 35 wt %, or about 2 wt % to about 70 wt %, or about 2 wt % to about 60 wt %, or about 2 wt % to about 50 wt %, or about 2 wt % to about 40 wt %, or about 2 wt % to about 37 wt %, or about 2 wt % to about 35 wt %, or about 5 wt % to about 70 wt %, or about 5 wt % to about 60 wt %, or about 5 wt % to about 50 wt %, or about 5 wt % to about 40 wt %, or about 5 wt % to about 37 wt %, or about 5 wt % to about 35 wt %, or about 10 wt % to about 70 wt %, or about 10 wt % to about 60 wt %, or about 10 wt % to about 50 wt %, or about 10 wt % to about 40 wt %, or about 10 wt % to about 37 wt %, or about 10 wt % to about 35 wt % (i.e., calculated on an oxide basis).

For example, when cobalt is included as a catalytic metal, the catalyst desirably includes cobalt in an amount totaling from about 1% to about 70% by weight (on an oxide basis) of total catalyst material. In certain embodiments, the total amount of the cobalt in the catalyst material is in the range of about 1 wt % to about 60 wt %, or about 1 wt % to about 55 wt %, or about 1 wt % to about 50 wt %, or about 1 wt % to about 40 wt %, or about 1 wt % to about 37 wt %, or about 1 wt % to about 35 wt %, or about 2 wt % to about 70 wt %, or about 2 wt % to about 60 wt %, or about 2 wt % to about 50 wt %, or about 2 wt % to about 40 wt %, or about 2 wt % to about 37 wt %, or about 2 wt % to about 35 wt %, or about 5 wt % to about 70 wt %, or about 5 wt % to about 60 wt %, or about 5 wt % to about 50 wt %, or about 5 wt % to about 40 wt %, or about 5 wt % to about 37 wt %, or about 5 wt % to about 35 wt %, or about 10 wt % to about 70 wt %, or about 10 wt % to about 60 wt %, or about 10 wt % to about 50 wt %, or about 10 wt % to about 40 wt %, or about 10 wt % to about 37 wt %, or about 10 wt % to about 35 wt % (i.e., calculated on an oxide basis).

In other embodiments, the catalytic metal can be iron or ruthenium, present, for example, in an amount as described above with respect to cobalt.

The person of ordinary skill in the art will appreciate that the catalytic metal is desirably in a substantially reduced state at the time of use in a Fischer-Tropsch synthesis. However, it will be understood that the catalytic metal can be present in the form of a metal compound, such as a metal oxide, a metal hydroxide, and the like. Oxide and/or hydroxide forms can be especially convenient for synthesis, transport and storage of the catalyst material. Reduction to reduced state can be performed in situ as a step in the Fischer-Tropsch synthesis process itself.

Optionally, the catalyst materials described herein can also include at least one promoter known to those skilled in the art. The promoter may vary according to the catalytic metal. A promoter can be an element that also, in an active form, has catalytic activity in the absence of the catalytic metal. Such an element will be termed herein a promoter when it is present in the catalyst in a lesser wt % than the catalytic metal.

A promoter preferably enhances the performance of the catalyst. Suitable measures of the performance that may be enhanced include selectivity, activity, stability, lifetime, reducibility and resistance to potential poisoning by impurities such as sulfur, nitrogen, and oxygen. A promoter is desirably a Fischer-Tropsch promoter, which is an element or compound that enhances the performance of a Fischer-Tropsch catalyst in a Fischer-Tropsch process.

It will be understood that as contemplated herein an enhanced performance of a promoted catalyst can be calculated according to any suitable method known to one of ordinary skill in the art. In particular, an enhanced performance can be given as a percent and computed as the ratio of the performance difference to the performance of a reference catalyst. The performance difference is between the performance of the promoted catalyst and the reference catalyst, wherein the reference catalyst is a similar corresponding catalyst having the nominally same amounts, e.g. by weight percent, of all components except the promoter. It will further be understood that as contemplated herein a performance can be measured in any suitable units. For example, when the performance is productivity, productivity can be measured in grams product per hour per liter reactor volume, grams product per hour per kilogram catalyst, and the like.

Suitable promoters vary with the catalytic metal and can be selected from Groups 1-15 of the Periodic Table of the Elements. A promoter can be in elemental form. Alternatively, a promoter can be present in an oxide compound. Further, a promoter can be present in an alloy containing the catalytic metal. Except as otherwise specified herein, a promoter is preferably present in an amount to provide a weight ratio of elemental promoter:elemental catalytic metal of from about 0.00005:1 to about 0.5:1, preferably from about 0.0005:1 to about 0.25:1 (dry basis). When the promoter comprises a metal from Groups 7, 8, 9, and 10 of the Periodic Table such as rhenium, ruthenium, platinum, or palladium, the weight ratio of elemental promoter:elemental catalytic metal may be between about 0.00005:1 and about 0.05:1.

Further, when the catalytic metal is cobalt or iron, suitable promoters include Group 1 elements such as potassium (K), lithium (Li), sodium (Na), and cesium (Cs); Group 2 elements such as calcium (Ca), magnesium (Mg), strontium (Sr), and barium (Ba); Group 3 elements such as scandium (Sc), yttrium (Y), and lanthanum (La); Group 4 elements such as titanium (Ti), zirconium (Zr), and hafnium (Hf); Group 5 elements such as vanadium (V), niobium (Nb), and tantalum (Ta); Group 6 elements such as molybdenum (Mo) and tungsten (W); Group 7 elements such as rhenium (Re) and manganese (Mn); Group 8 elements such as ruthenium (Ru) and osmium (Os); Group 9 elements such as rhodium (Rd) and iridium (fr); Group 10 elements such as platinum (Pt) and palladium (Pd); Group 11 elements such as silver (Ag) and copper (Cu); Group 12 elements such as zinc (Zn), cadmium (Cd), and mercury (Hg); Group 13 elements such as gallium (Ga), indium (In), thallium (Tl), and boron (B); Group 14 elements such as tin (Sn) and lead (Pb); and Group 15 elements such as phosphorus (P), bismuth (Bi), and antimony (Sb).

When the catalytic metal is cobalt, iron, or combinations thereof, the promoter can be selected from, for example, platinum, palladium, ruthenium, rhenium, silver, boron, copper, lithium, sodium, potassium, magnesium, manganese, or combinations thereof.

In certain embodiments, when the catalytic metal is cobalt, the promoter is rhenium, ruthenium, platinum, palladium, boron, silver, or a combination thereof. When the promoter includes rhenium, the rhenium can be present in the catalyst material in an amount, for example, between about 0.001 and about 5% by weight, between about 0.01 and about 2% by weight, or between about 0.2 and about 1% by weight. When the promoter includes ruthenium, the ruthenium can be present in the catalyst material, for example, in an amount between about 0.0001 and about 5% by weight, between about 0.001 and about 1% by weight, or between about 0.01 and about 1% by weight. When the promoter includes platinum, the platinum can be present in the catalyst material, for example, in an amount between about 0.00001 and about 5% by weight, more preferably between about 0.0001 and about 1% by weight, and most preferably between about 0.0005 and about 1% by weight. When the promoter includes palladium, the palladium can be present in the catalyst material, for example, in an amount between about 0.00001 and about 5% by weight, between about 0.0001 and about 2% by weight, or between about 0.0005 and about 1% by weight. When the promoter includes silver, the silver can be present in an amount, for example, from about 0.01 to about 10 wt % silver, from about 0.07 to about 7 wt % silver, or about 0.1 to about 5 wt % silver. When the promoter includes boron, the boron can be present in the catalyst material, for example, in an amount of from about 0.025 to about 2 wt % boron, from about 0.05 to about 1.8 wt % boron, or from about 0.075 to about 1.5 wt % boron. Amounts of all such promoters are calculated on an oxide basis.

By way of example and not limitation, when the catalytic metal is iron, suitable promoters include copper (Cu), potassium (K), silicon (Si), zirconium (Zr), silver (Ag), lithium (Li), sodium (Na), rubidium (Rb), cesium (Cs), magnesium (Mg), manganese (Mn), calcium (Ca), strontium (Sr), and barium (Ba). In certain embodiments, when the catalytic metal is iron, the promoter can include potassium, copper, lithium, sodium, silver, magnesium, or combinations thereof. When the catalytic metal is iron, the catalyst may include potassium or lithium as a promoter; and alternatively or in combination, the catalyst may include copper or silver. When the catalyst material comprises lithium as a promoter, lithium can be present, for example, in an amount between about 0.05 wt % and about 5 wt % of lithium, or between about 0.5 wt % and about 2 wt %. When the catalyst material includes silver as a promoter, silver can be present, for example, in an amount between about 0.001 wt % and about 5 wt % of silver; or between about 0.001 wt % and about 2 wt % of silver; or between about 0.005 wt % and 1 wt % of silver. When the catalyst material includes potassium as a promoter, potassium can be present, for example, in an amount between about 0.0001 wt % and about 10 wt % of potassium; or between about 0.0005 wt % and about 1 wt % of potassium; or between about 0.0005 wt % and about 0.5 wt % of potassium. When the catalyst material comprises calcium as a promoter, calcium can be present, for example, in an amount between about 0.001 wt % and about 4 wt % of calcium; or between about 0.5 wt % and about 3 wt % of calcium. When the catalyst material comprises copper as a promoter, copper can be present, for example, in an amount between about 0.1 wt % and about 10 wt % copper. Amounts of all such promoters are calculated on an oxide basis.

Alternatively, by way of example and not limitation, when the catalytic metal is ruthenium, suitable promoters include rhenium. When the ruthenium catalyst includes rhenium, the rhenium can be present, for example, in the catalyst material in an amount between about 0.001 and about 1% by weight, or between about 0.01 and about 0.5% by weight, or between about 0.05 and about 0.5% by weight. Amounts of all such promoters are calculated on an oxide basis.

Similarly, the person of ordinary skill in the art will appreciate that a variety of support materials can be used in the catalysts described herein. The support is typically a porous carrier that provides mechanical strength and a high surface area on which the catalytic metal and any promoter(s) may be deposited. Catalyst supports for catalysts used in Fischer-Tropsch synthesis of hydrocarbons can be, for example, refractory oxides (e.g., silica, alumina, titania, zirconia or mixtures thereof). In one embodiment, the support is an aluminum oxide. Various aluminum oxides are suitable for use as support materials. For example, gamma-alumina is an oxide compound of aluminum having, in its pure form, the empirical formula $\gamma$-$Al_2O_3$. $\gamma$-Alumina distinguished from other polymorphic forms of alumina, such as alpha-alumina ($\alpha$-$Al_2O_3$), by its structure, which may be detected for example by x-ray diffraction or electron microscopy. The structure of $\gamma$-alumina is conventionally thought to approximate a spinel with a cubic form or a tetragonal form or combination. In certain embodiments, the support is aluminum oxide combined with silicon oxide, for example, as described in U.S. Pat. No. 7,341,976, which is hereby incorporated herein by reference in its entirety for all purposes.

The catalysts may be prepared using any suitable method. Without limitation, examples of suitable methods include impregnating a catalytic metal onto a support, extruding the support material with the catalytic metal to prepare catalyst extrudates, spray-drying the catalytic metal and the support material from a liquid medium containing both, and/or precipitating the catalytic metal onto the support material. The catalyst materials may be used in the form of powders, particles, pellets, monoliths, honeycombs, packed beds, foams, and aerogels. The most preferred method of preparation may vary among those skilled in the art depending, for example, on the desired catalyst particle size. Those skilled in the art are able to select the most suitable method for a given set of requirements.

The catalyst can be formed in a variety shapes. For example, for use in fluidized or slurry systems, the catalyst can be formed as a plurality of discrete porous particles. The discrete porous particles can be formed in a variety of particle sizes and distributions. For example, in certain embodiments, the discrete particles have an average discrete particle size in the range of about 10 μm to about 300 μm. In various other embodiments, the discrete porous particles have an average discrete particle size in the range of about 10 to 200 μm, or about 10 μm to about 150 μm, or about 10 μm to about 100 μm, or about 30 μm to about 200 μm, or about 30 μm to about 150 μm, or about 30 μm to about 100 μm, or about 50 μm to about 200 μm, or about 50 μm to about 150 μm, or about 50 μm to about 100 μm. The discrete porous articles can be, for example, substantially spheroidal in shape, as would result from a spray drying process. The person of ordinary skill in the art can tune the spray drying process (and other processes used in the manufacture) to provide the desired particle shape and size.

The catalysts described herein can be provided with a variety of different pore volumes, depending, e.g., on the processes used for making them and the desired end use. For example, in certain embodiments, a catalyst material as described herein has a pore volume within the range of about 0.05 to about 1.0 $cm^3/g$, or about 0.05 to about 0.8 $cm^3/g$, or about 0.05 to about 0.6 $cm^3/g$, or about 0.1 to about 1.0 $cm^3/g$, or about 0.1 to about 0.8 $cm^3/g$, or about 0.1 to about 0.6 $cm^3/g$, or about 0.2 to about 1.0 $cm^3/g$, or about 0.2 to about 0.8 $cm^3/g$, or about 0.2 to about 0.6 $cm^3/g$, or about 0.3 to about 1.0 $cm^3/g$, or about 0.3 to about 0.8 $cm^3/g$, or about 0.3 to about 0.6 $cm^3/g$, or about 0.3 to about 0.5 $cm^3/g$. The person of ordinary skill in the art can, in view of the processes described herein, provide a desired pore volume to a catalyst. Pore volumes are measured by Hg porisometry, and provide the total volume or pores below 5000 Å in size. The person of ordinary skill in the art can, in view of the processes described herein, provide a desired pore volume to a catalyst support material.

Similarly, the catalysts described herein can be provided with a variety of different surface areas, depending, e.g., on the processes used for making them and the desired end use. The surface areas are measured using the Brunauer-Emmett-Teller (BET) Surface Area method. In certain embodiments, a catalyst as described herein has a surface area within the range of from about 10 to about 300 $m^2/g$, or about 25 to about 300 $m^2/g$, or about 50 to about 300 $m^2/g$, or about 100 to about 300 $m^2/g$, or about 10 to about 200 $m^2/g$, or about 25 to about 200 $m^2/g$, or about 50 to about 200 $m^2/g$, or about 100 to about 200 $m^2/g$, or about 10 to about 150 $m^2/g$, or about 25 to about 150 $m^2/g$, or about 50 to about 150 $m^2/g$, or about 100 to about 150 $m^2/g$. The person of ordinary skill in the art can, in view of the processes described herein, provide a desired surface area to a catalyst.

The catalyst is disposed in a first organic material. The organic material can be, for example, the organic material from a Fischer-Tropsch reactor. Such organic materials can be, for example, substantially a mixture of Fischer-Tropsch reaction products. As the person of ordinary skill in the art will appreciate, the catalyst may be provided to the Fischer-Tropsch process in combination with a protective coating, as described in U.S. Pat. No. 7,179,766, which is hereby incorporated herein by reference in its entirety. Thus, the organic material may include a minor amount of the material of the protective coating (e.g., epoxy resin, fatty acids, fatty alcohols, fatty esters, fatty stearates, hydrocarbon resins, microcrystalline paraffins, paraffin wax, synthetic wax, polyesters, polyethylene glycol, polyethylene waxes, polyglycols, polyvinyl alcohols, polystyrene, vegetable waxes, a wax obtained from processes using coal, natural gas, biomass, or methanol as feedstock, wax blends and combinations thereof) in addition to the Fischer-Tropsch reaction product.

The first organic material may be, for example, substantially waxy at room temperature. The first organic material can have, for example, a congealing point in the range of about 60° C. to about 120° C., or about 60° C. to about 100° C., or about 60° C. to about 80° C., or about 80° C. to about 120° C., or about 80° C. to about 100° C., or about 100° C. to about 120° C.

As noted above, the organic material can be the organic material from a Fischer-Tropsch reactor. For example, the media inside a bubble column reactor generally includes a slurry of the catalyst in organic material (primarily Fischer-Tropsch reaction products). Thus, the method can further include obtaining the catalyst disposed in the first organic material from a Fischer-Tropsch reaction process. As the person of ordinary skill in the art will appreciate, the catalyst disposed in the first organic material can be transferred to a separate vessel or reactor system for the performance of the methods described herein.

As described above, in various aspects of the methods described herein a substantial portion all of the first organic material is removed from the catalyst to provide a dewaxed catalyst having less than about 40 wt % organic material disposed thereon. For example, in certain embodiments, a substantial portion of the first organic material is removed from the catalyst to provide a dewaxed catalyst having less than about 20 wt % organic material disposed thereon.

Figure 2:
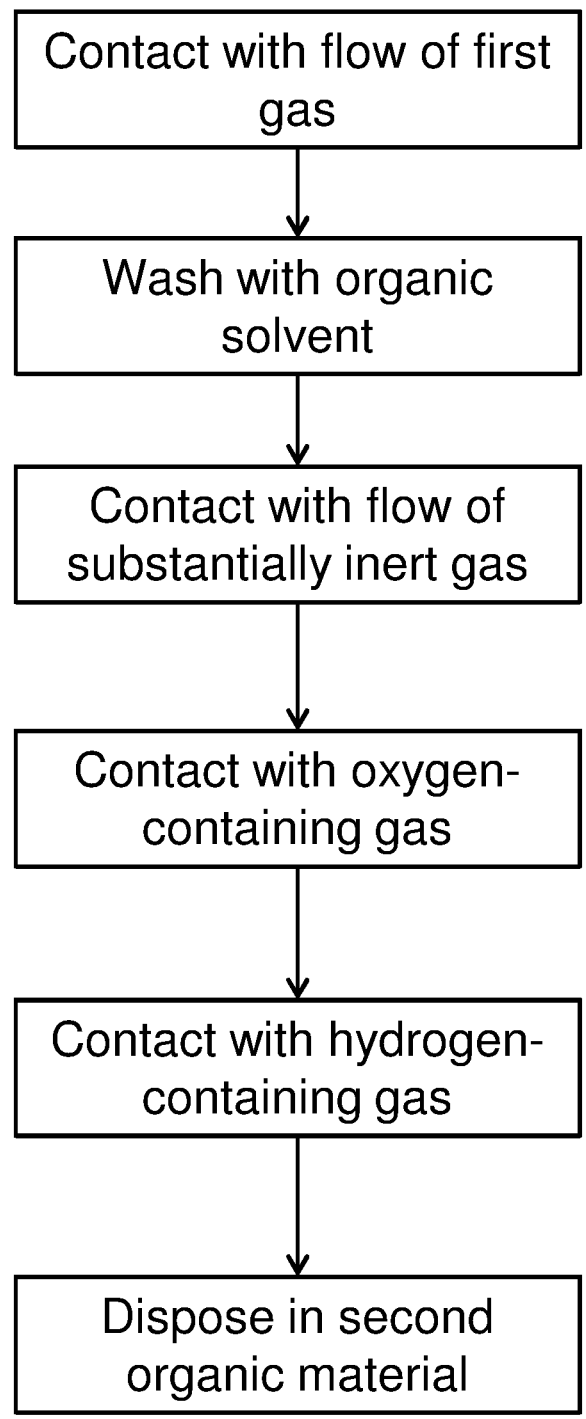
FIG. 2 is a flowchart of a process according to another embodiment of the disclosure.

In certain embodiments, and as shown in the flowchart view of FIG. 2, the removing the substantial portion of the first organic material from the catalyst to provide a dewaxed catalyst includes contacting the catalyst disposed in the first organic material with a flow of a first gas at a temperature of at least about 70° C. This contacting with the flow of the first gas can be performed so as to remove a major fraction of the first organic material from the catalyst, e.g., by substantially volatilizing or mobilizing the first organic material. In certain embodiments, the first organic material is in a liquid or slurry phase at the temperature of the contacting the catalyst with the flow of the first gas.

As the person of ordinary skill in the art will appreciate, a wide variety of gases can be used as the first gas. The first gas can be, for example, a substantially inert gas, e.g., nitrogen. In other embodiments, the first gas includes an inert gas mixed with hydrogen, oxygen or air. For example, in one embodiment, the first gas includes oxygen (i.e., from air or from another oxygen source), e.g., in an amount of no more than about 10 vol %, no more than about 5 vol % or no more than about 1 vol %. In certain embodiments, the first gas is substantially free of oxygen. In other embodiments, the first gas includes hydrogen. Examples of gases suitable for use as the first gas include, for example, nitrogen, helium, carbon monoxide, light hydrocarbons such as methane. In certain embodiments, the first gas is substantially free of moisture.

The contacting of the catalyst disposed in the first organic material with the flow of the first gas can be performed at a variety of temperatures. Desirably, the temperature is sufficient to volatilize or mobilize the first organic material; this temperature will vary with the pressure at which the contacting with the first gas is performed. In certain desirable embodiments, the temperature is not so high as to substantially combust or pyrolyze the first organic material. In certain embodiments, the contacting of the catalyst disposed in the first organic material with the flow of the first gas is performed at a temperature in the range of about 70° C. to about 300° C., or about 70° C. to about 200° C., or about 70° C. to about 150° C., or about 100° C. to about 300° C., or about 100° C. to about 200° C., or about 100° C. to about 150° C., or about 125° C. to about 300° C., or about 125° C. to about 200° C.

The contacting of the catalyst disposed in the first organic material with the flow of the first gas can be performed at a variety of pressures. For example, the contacting of the catalyst disposed in the first organic material with the flow of the first gas can be performed under vacuum, or at atmospheric pressure, or at a positive pressure. In other embodiments, the contacting of the catalyst disposed in the first organic material with the flow of the first gas can be performed under vacuum pressure. For example, in certain embodiments, the contacting of the catalyst disposed in the first organic material with the flow of the first gas can be performed at an absolute pressure (i.e., relative to vacuum, with standard atmospheric pressure being 101.3 kPa) in the range of about 1 kPa to about 2500 kPa, or about 10 kPa to about 2500 kPa, or about 50 kPa to about 2500 kPa, or about 90 kPa to about 2500 kPa, or about 250 kPa to about 2500 kPa, or about 500 kPa to about 2500 kPa, or about 1 kPa to about 1000 kPa, or about 10 kPa to about 1000 kPa, or about 50 kPa to about 1000 kPa, or about 90 kPa to about 1000 kPa, or about 250 kPa to about 1000 kPa, or about 500 kPa to about 1000 kPa, or about 1 kPa to about 500 kPa, or about 10 kPa to about 500 kPa, or about 50 kPa to about 500 kPa, or about 90 kPa to about 500 kPa, or about 250 kPa to about 500 kPa, or about 1 kPa to about 110 kPa, or about 10 kPa to about 110 kPa, or about 50 kPa to about 110 kPa.

In certain such embodiments (e.g., as shown in the flowchart view of FIG. 2), removing a substantial portion of the first organic material from the catalyst to provide the dewaxed catalyst includes, e.g., after contacting the catalyst with the flow of the first gas, washing the catalyst with an organic solvent, then optionally drying the catalyst. The organic solvent can take many forms, as the person of ordinary skill in the art will appreciate, depending on the identity of the first organic material. The organic solvent is desirably a good solvent for the first organic material. For example, in certain embodiments, the organic solvent is a hydrocarbon organic solvent, such as xylene, toluene, hexane, heptane, petroleum ether or heavy naphtha.

The washing of the catalyst with the organic solvent can be performed under a variety of conditions. For example, the washing of the catalyst with the organic solvent can be performed at variety of temperatures, e.g., at ambient temperature, or at a temperature in the range of about 20° C. to about 125° C. The washing of the substantially dewaxed catalyst with the organic solvent can be performed at a variety of gauge pressures, for example, at atmospheric pressure, or under a positive pressure, e.g., at gauge pressures up to about 1500 kPa.

The washing of the substantially dewaxed catalyst can be performed in the presence of a flow of a second gas. The second gas can be, for example, an air or an inert gas, e.g., nitrogen, helium, carbon dioxide and light hydrocarbon such as methane. In other embodiments, the second gas is an air or an inert gas mixed with hydrogen, oxygen or air. For example, in one embodiment, the second gas includes oxygen (i.e., from air or from another oxygen source), e.g., in an amount of no more than 20 vol %. In certain embodiments, the second gas is substantially free of oxygen. In other embodiments, the second gas is an inert gas mixed with hydrogen. In certain embodiments, the second gas is substantially free of moisture (e.g., less than 5 vol %, less than 1 vol % or less than 0.5 vol % water). The second gas can be, for example, bubbled through the organic solvent.

As noted above, after the catalyst is washed, it can be dried to remove a substantial portion of any residual solvent, for example, using a flow of a third gas (e.g., under vacuum pressure, at atmospheric pressure, or at a positive pressure). The third gas can be, for example, an inert gas. Vacuum evaporation can also be used to dry the catalyst. Drying can be performed at a variety of temperatures. But in other embodiments, residual solvent is removed by the contacting with substantially inert gas described below.

Of course, in certain embodiments, the catalyst is not washed with an organic solvent or treated with supercritical $CO_2$. In such embodiments, the dewaxed catalyst can proceed directly (e.g., from contact with the flow of the first gas) to contact with the substantially inert gas, as described in more detail below.

As described above, the dewaxed catalyst is contacted with a flow of substantially inert gas at a temperature of at least about 200° C. to provide an inert gas-treated catalyst having less than about 10 wt % organic material disposed thereon. Notably, contacting with the substantially inert gas can substantially reduce the amount of organic material disposed on the catalyst to a sufficiently low amount that highly exothermic reaction is avoided in the subsequent oxygen treatment step. In certain embodiments, the dewaxed catalyst is contacted with a flow of substantially inert gas at a temperature of at least about 200° C. to provide an inert gas-treated catalyst having less than about 5 wt %, less than about 3 wt %, less than about 2 wt % or even less than about 1 wt % organic material disposed thereon. The contacting with the substantially inert gas is desirably performed under conditions under which substantially no combustion or pyrolysis of organic material occurs.

The contacting with the flow of the substantially inert gas may be performed at a variety of temperatures; for example, in certain embodiments, the contacting with the flow of the substantially inert gas is performed at a temperature in the range of about 200° C. to about 600° C., or about 300° C. to about 600° C., or about 400° C. to about 600° C., or about 200° C. to about 500° C., or about 300° C. to about 500° C., or about 400° C. to about 500° C., or about 200° C. to about 450° C., or about 300° C. to about 450° C.

The contacting with the flow of the substantially inert gas can be performed at a variety of pressures, for example, at atmospheric pressure, or under a positive pressure, e.g., at an absolute pressure in the range of about 1 kPa to about 2500 kPa, or about 10 kPa to about 2500 kPa, or about 50 kPa to about 2500 kPa, or about 90 kPa to about 2500 kPa, or about 250 kPa to about 2500 kPa, or about 500 kPa to about 2500 kPa, or about 1 kPa to about 1000 kPa, or about 10 kPa to about 1000 kPa, or about 50 kPa to about 1000 kPa, or about 90 kPa to about 1000 kPa, or about 250 kPa to about 1000 kPa, or about 500 kPa to about 1000 kPa, or about 1 kPa to about 500 kPa, or about 10 kPa to about 500 kPa, or about 50 kPa to about 500 kPa, or about 90 kPa to about 500 kPa, or about 250 kPa to about 500 kPa, or about 1 kPa to about 110 kPa, or about 10 kPa to about 110 kPa, or about 50 kPa to about 110 kPa.

The substantially inert gas can be, for example, an inert gas, e.g., nitrogen, helium, carbon dioxide or a light hydrocarbon such as methane. In other embodiments, the substantially inert gas includes a small amount of hydrogen, oxygen or air. For example, in one embodiment, the substantially inert gas includes oxygen (i.e., from air or from another oxygen source), e.g., in an amount of no more than about 5 vol % or no more than about 1 vol %, or no more than about 0.1 vol %, or no more than about 0.01 vol %. In certain embodiments, the substantially inert gas is substantially free of oxygen. In other embodiments, the substantially inert gas is an inert gas mixed with hydrogen (e.g., in an amount of no more than about 5 vol % or no more than about 1 vol %). In certain embodiments, the substantially inert gas is substantially free of moisture (e.g., less than 5 vol %, less than 1 vol % or less than 0.5 vol % water).

The inert gas-treated catalyst is then contacted with an oxygen-containing gas at a temperature of at least 200° C. to form an oxidized catalyst. The oxygen-containing gas desirably includes oxygen in a sufficient quantity to oxidize any residual organic material on the catalyst. The oxygen treatment can be performed, for example, to reduce the amount of carbonaceous material disposed on the catalyst to less than about 2%, less than about 1%, less than about 0.5%, or even less than about 0.1%. This oxygen treatment step can also oxidize catalytic metal or a promoter to a desired state.

A variety of amounts of oxygen can be present in the oxygen-containing gas. For example, the oxygen-containing gas can include in the range of about 0.02 vol % to about 25 vol %, or about 0.02 vol % to about 15 vol %, or about 0.02 vol % to about 10 vol %, or about 0.1 vol % to about 25 vol %, or about 0.1 vol % to about 15 vol %, or about 0.1 vol % to about 10 vol %, or about 1 vol % to about 25 vol %, or about 1 vol % to about 15 vol %, or about 1 vol % to about 10 vol %, or about 2 vol % to about 25 vol %, or about 2 vol % to about 15 vol %, or about 2 vol % to about 10 vol % oxygen. The oxygen concentration of the oxygen-containing gas can be increased during the contacting.

The contacting with the oxygen-containing gas may be performed at a variety of temperatures of at least about 200° C., or at least about 250° C., or even at least about 300° C. For example, in certain embodiments, the contacting with the flow of the oxygen-containing gas is performed at a temperature in the range of about 200° C. to about 600° C., or about 300° C. to about 600° C., or about 200° C. to about 500° C., or about 300° C. to about 500° C., or about 300° C. to about 400° C., or about 300° C. to about 350° C.

The contacting with the flow of the oxygen-containing gas can be performed at a variety of pressures. For example, the contacting can be performed at atmospheric pressure, or under a positive pressure, e.g., at gauge pressures up to about 1500 kPa.

In certain especially advantageous embodiments of the disclosed processes, the contacting with the oxygen-containing gas is performed with an increasing amount of oxygen, starting at an amount in the range of less than about 5 vol % and increasing (e.g., continuously or in steps) to greater than about 15 vol % oxygen. For example, the oxygen concentration at the beginning of the contacting with the oxygen-containing gas can be less than about 3 vol %, less than about 2 vol %, less than about 1 vol %, less than about 0.5 vol % or even less than about 0.05 vol %. The oxygen concentration at the end of the contacting with the oxygen-containing gas can be, for example, greater than about 18% oxygen or even greater than about 20% oxygen. In certain embodiments, mixtures of air or oxygen with an inert gas can be used as the oxygen-containing gas to provide various oxygen contents depending on the mixing ratio; air can be used at the end of the contacting with the oxygen-containing gas.

Advantageously, the contacting with increasing oxygen concentrations can be performed such that the temperature remains below 600° C., below 500° C., below 400° C., or even below 300° C. For example, in certain embodiments, the contacting with increasing oxygen concentrations is performed such that the temperature remains in the range of 250° C. to 400° C., 300° C. to 400° C., 250° C. or 350° C., or 300° C. to 350° C.

In certain embodiments, the contacting with increasing oxygen concentrations is performed such that the temperature of the catalyst does not increase more than about 100° C., more than about 50° C., more than about 40° C., more than about 30° C. or even more than about 20° C. during the contacting with the oxygen-containing gas.

In certain embodiments, when the increase in oxygen concentration is performed stepwise, each step in oxygen concentration can be performed such that the increase in catalyst temperature is no more than 3° C. per step.

In certain advantageous embodiments, the process can be monitored and controlled via temperature in order to provide the desired low temperature rise to the process. Accordingly, in certain embodiments, the process includes, during the contacting with the oxygen-containing gas, measuring the temperature of the catalyst and using the result of the temperature measurement to determine the rate of increase of the oxygen concentration. For example, when performing the increase in oxygen concentration in a stepwise manner, small changes in concentration can be used at first in order to determine what the change in temperature is with each change in oxygen concentration, then the change in oxygen concentration per step can be set accordingly. In any method, continuous or frequent temperature measurements can be used to speed up or slow down the rate of oxidation (e.g., via changing the amount of oxygen supplied to the process) in order to provide a reasonable rate of oxidation without causing an undesirable temperature increase. Directly monitoring temperature in this manner can advantageously protect the catalyst, as an exothermic temperature spike can damage the catalyst via sintering, change of the pore structure, or a reduction of surface area. For example, in certain embodiments, the temperature measurements can be fed to a processor programmed to determine a desirable change in oxygen concentration as a function of the measured temperature (e.g., such that the temperature of the catalyst remains below 600° C., below 500° C., below 400° C., or even below 300° C., or such that the temperature of the catalyst does not increase more than about 100° C., more than about 50° C., more than about 40° C., more than about 30° C. or even more than about 20° C. during the contacting with the oxygen-containing gas). The processor can be programmed to control (and can be used to control) the amount and/or concentration of the oxygen-containing process such that the process remains within any of the desirable temperature limitations described above (e.g., such that the temperature of the catalyst remains below 600° C., below 500° C., below 400° C., or even below 300° C., or such that the temperature of the catalyst does not increase more than about 100° C., more than about 50° C., more than about 40° C., more than about 30° C. or even more than about 20° C. during the contacting with the oxygen-containing gas). Alternatively, an operator can determine the appropriate changes in oxygen supplied to the process based on the temperature measurements, and adjust the oxygen flow accordingly (e.g., such that the temperature of the catalyst remains below 600° C., below 500° C., below 400° C., or even below 300° C., or such that the temperature of the catalyst does not increase more than about 100° C., more than about 50° C., more than about 40° C., more than about 30° C. or even more than about 20° C. during the contacting with the oxygen-containing gas).

In order to regenerate the catalytic metal to a substantially reduced form, the oxidized catalyst is contacted with a hydrogen-containing gas at a temperature of at least about 200° C. to form a regenerated catalyst. The hydrogen-containing gas desirably includes sufficient hydrogen regenerate the catalyst. For example, in certain embodiments, the hydrogen-containing gas includes at least about 10 vol %, at least about 20 vol %, at least about 40 vol %, or at least about 60 vol % hydrogen. In certain embodiments, the hydrogen-containing gas consists essentially of hydrogen.

The contacting with the hydrogen-containing gas may be performed at a variety of temperatures of at least about 200° C., or even of at least about 300° C. For example, in certain embodiments, the contacting with the hydrogen-containing gas is performed at a temperature in the range of about 200° C. to about 600° C., or about 300° C. to about 600° C., or about 200° C. to about 500° C., or about 300° C. to about 500° C., or about 300° C. to about 400° C.

The contacting with the hydrogen-containing gas can be performed at a variety of pressures. For example, the contacting can be performed at a gauge pressure in the range of up to about 1500 kPa, or up to about 1000 kPa, or up to about 500 kPa.

The catalytic metal of the regenerated catalyst in many embodiments is in a substantially reduced form. For example, in certain embodiments, at least about 20 mol %, at least about 30 mol %, at least about 40 mol %, at least about 50 mol %, or even at least about 60 mol % of the catalytic metal is in a zero-valent oxidation state. In certain such embodiments, up to about 90 mol %, up to about 95 mol %, or even up to about 99 mol % of the catalytic metal is in a zero-valent state. The contacting with the hydrogen-containing gas can be performed to provide the catalyst metal in a desirable substantially-reduced form, for example, by monitoring hydrogen consumption or water formation to determine the process endpoint.

Regenerated catalysts can often be unstable in air, for example, due to pyrophoricity and/or susceptibility to oxidation. Accordingly, the processes described herein further include disposing the regenerated catalyst in a second organic material. The second organic material can be, for example, selected from epoxy resin, fatty acids, fatty alcohols, fatty esters, fatty stearates, hydrocarbon resins, microcrystalline paraffins, synthetic wax, paraffin wax, polyesters, polyethylene glycol, polyethylene waxes, polyglycols, polyvinyl alcohols, polystyrene, vegetable waxes, a wax obtained from processes using coal, natural gas, biomass, or methanol as feedstock, a synthetic wax produced from a Fischer-Trospch reaction, wax blends and combinations thereof. The second organic material can have, for example, a congealing point in the range of about 40° C. to about 125° C., or about 40° C. to about 100° C., or about 40° C. to about 80° C., or about 60° C. to about 125° C., or about 60° C. to about 100° C., or about 60° C. to about 80° C., or about 80° C. to about 125° C., or about 40° C. to about 100° C.

The second organic material can thus protect the catalyst from air during transport and loading into a reactor. The mixture of the catalyst and the second organic material can be formed into pastilles or flakes, as described, for example, in U.S. Pat. No. 7,179,766, which is hereby incorporated herein by reference in its entirety.

The regeneration processes described herein can be performed by the person of ordinary skill in the art using conventional equipment and techniques. The person of ordinary skill in the art will appreciate that various process steps of such regeneration processes can be carried out in one reactor or separate reactors. For example, as the oxidized catalyst can be pyrophoric, in certain embodiments the contacting with the oxygen-containing gas and the contacting with the hydrogen-containing gas is carried out in the same reactor. Reactors can be in any suitable configuration, e.g., fluidized bed, fixed bed or moving bed. Various process steps can be carried out as continuous processes or as batch processes.

The regenerated catalysts described herein may be used to facilitate any reaction requiring a reduced metal catalyst. That is, the catalyst may be used with various reactants to promote the production of different products. In some embodiments, the catalyst described above is used in a process for producing synthesis gas or in a Fischer-Tropsch process for synthesizing hydrocarbons and/or alcohols, depending especially on the identity and state of the catalytic metal. Accordingly, in one embodiment, the process described herein further includes disposing the regenerated catalyst in the second organic material in a reactor (e.g., configured to carry out one of these synthetic processes).

The processes described herein can provide catalysts with improved properties over prior art catalysts. Accordingly, another aspect of the disclosure is a regenerated catalyst made by a process as described herein.

Another aspect of the disclosure is a process for producing one or more hydrocarbons, e.g., by the Fischer-Tropsch reaction. One embodiment of such a process includes contacting carbon monoxide and hydrogen with a catalyst made as described herein.

Mixtures of hydrogen and carbon monoxide suitable as a feedstock for conversion to hydrocarbons according to the processes described herein can be obtained from light hydrocarbons such as methane by means of steam reforming, partial oxidation, or other processes known in the art. Desirably, the hydrogen is provided in the feedstock as free hydrogen, although some Fischer-Tropsch catalyst materials have sufficient water gas shift activity to convert some water and carbon monoxide to hydrogen and carbon dioxide, thus producing hydrogen in situ for use in the Fischer-Tropsch process. In certain embodiments, the molar ratio of hydrogen to carbon monoxide when contacted with the catalyst material greater than 0.2:1 (e.g., from about 0.67 to 2.5). In certain embodiments, for example, when cobalt, nickel, and/or ruthenium catalysts are used, the hydrogen and carbon monoxide are present in a molar ratio of about 1.4:1 to 2.3:1, when contacted with the catalyst material. In certain embodiments, for example, when iron catalysts are used, the hydrogen and carbon monoxide are present in a molar ratio of about 0.24:1 and 2.3:1, when contacted with the catalyst material. As the person of ordinary skill in the art will appreciate, various other substances can be present, such as water, carbon dioxide, and/or hydrocarbonaceous products of the Fischer-Tropsch reaction. Desirably, only a low concentration (if any) compounds or elements that have a deleterious effect on the catalyst, such as poisons, should be present. For example, the feed gas may need to be pretreated to ensure that it contains low concentrations of sulfur or nitrogen compounds such as hydrogen sulfide, ammonia, hydrogen cyanide, and carbonyl sulfides.

The carbon monoxide and the hydrogen can be contacted with the catalyst material in a reaction zone. As the person of ordinary skill in the art will appreciate, the reaction zone can take many physical forms. Mechanical arrangements of conventional design may be employed as the reaction zone including, for example, plug flow, continuous stirred tank, fixed bed, fluidized bed, slurry phase, slurry bubble column, reactive distillation column, or ebulliating bed reactors, among others. The size and physical form of the catalyst may vary, depending on the reactor in which it is to be used. Plug flow, fluidized bed, reactive distillation, ebulliating bed, and continuous stirred tank reactors have been delineated in "Chemical Reaction Engineering," by Octave Levenspiel, and are known in the art, as are slurry bubble columns. In one particular embodiment, the reaction zone is a slurry bubble column. One particular slurry bubble column is described in United States Patent Application Publication 2003/0114543, which is hereby incorporated herein by reference in its entirety.

When the reaction zone includes a slurry bubble column, the column can include, for example, a three-phase slurry (i.e., a solid phase including at least the catalyst material; a liquid phase including at least a hydrocarbon fluid; and a gas phase including at least the carbon monoxide and the hydrogen, optionally together with a gas inert to the Fischer-Tropsch reaction). For example, a process as described herein performed in a slurry bubble column preferably includes dispersing the particles of the catalyst in a liquid phase including the hydrocarbons to form a two-phase slurry and dispersing the hydrogen and carbon monoxide in the two-phase slurry to form the three-phase slurry. The slurry bubble column can include, for example, a vertical reactor, and dispersal desirably includes injection of the gas into the bottom half of the reactor.

The Fischer-Tropsch process may be typically run in a continuous mode. In this mode, the gas hourly space velocity through the reaction zone can range, for example, from about 50 to about 10,000 $hr^{-1}$, or from about 300 $hr^{-1}$ to about 2,000 $hr^{-1}$. The gas hourly space velocity is defined as the volume of reactants per time per reaction zone volume. The volume of reactant gases is determined at (or extrapolated to) standard conditions (standard pressure of 101 kPa and standard temperature of 0° C.). The reaction zone volume is defined by the portion of the reaction vessel volume where the reaction takes place and which is occupied by a gaseous phase comprising reactants, products and/or inerts; a liquid phase comprising liquid/wax products and/or other liquids; and a solid phase comprising the catalyst material. The temperature at which the hydrogen and carbon monoxide are contacted with the catalyst material (e.g., the reaction zone temperature) may vary, as would be apparent to the person of ordinary skill in the art. For example, the temperature at which the hydrogen and carbon monoxide are contacted with the catalyst material (e.g., the reaction zone temperature) may be in the range from about 160° C. to about 350° C.; or from about 190° C. to about 260° C., or from about 205° C. to about 250° C. The pressure at which the contacting of the hydrogen and carbon monoxide with the catalyst material (e.g., the reaction zone pressure) is performed can be, for example, in the range of about 80 psia (552 kPa) to about 1000 psia (6,895 kPa), or from 80 psia (552 kPa) to about 800 psia (5,515 kPa), or from about 140 psia (965 kPa) to about 750 psia (5,170 kPa), or from about 250 psia (1,720 kPa) to about 650 psia (4,480 kPa).

The products resulting from the process may have a great range of molecular weights. Typically, the carbon number range of the product hydrocarbons may start at methane and continue to about 50 to 100 carbons or more per molecule as measured by current analytical techniques. The process is particularly useful for making hydrocarbons having five or more carbon atoms, especially when the above-referenced preferred space velocity, temperature and pressure ranges are employed.

Typically, in the Fischer-Tropsch synthesis, the product spectra can be described by likening the Fischer-Tropsch reaction to a polymerization reaction with a Shultz-Flory chain growth probability, called alpha value ($\alpha$), that is independent of the number of carbon atoms in the lengthening molecule. The alpha value is typically interpreted as the ratio of the mole fraction of the $C_{n+1}$ product to the mole fraction of the $C_n$ product. An alpha value of at least 0.72 is desirable for producing high carbon-length hydrocarbons, such as those of diesel cuts.

The wide range of hydrocarbons produced can afford liquid phase products under the reaction conditions. Therefore, the effluent stream of process may be a mixed phase stream including liquid and gas phase products. The effluent gaseous stream of the reaction zone can be cooled to condense additional amounts of hydrocarbons and can be passed into a vapor-liquid separation zone separating the liquid and vapor phase products. The gaseous material can be passed into a second stage of cooling for recovery of additional hydrocarbons. The liquid material from the reaction zone together with any liquid from a subsequent separation zone can be fed into a fractionation column. In an embodiment, a stripping column is employed first to remove light hydrocarbons such as propane and butane. The remaining hydrocarbons can be passed into a fractionation column in which they are separated by boiling point range into products such as naphtha, kerosene and fuel oils. Hydrocarbons recovered from the reaction zone and having a boiling point above that of the desired products can be passed into conventional processing equipment such as a hydrocracking zone in order to reduce their molecular weight to that of desired products such as middle distillates and gasoline. The gas phase recovered from the reactor zone effluent stream after hydrocarbon recovery can be partially recycled if it contains a sufficient quantity of hydrogen and/or carbon monoxide.

We claim:
1. A process for regenerating a deactivated catalyst, the catalyst being disposed in a first organic material, the catalyst comprising a catalytic metal disposed on a support, the process comprising
 removing a substantial portion of the first organic material from the catalyst to provide a dewaxed catalyst having less than about 40 wt % organic material disposed thereon;
 contacting the dewaxed catalyst with a flow of a substantially inert gas at a temperature of at least about 200° C. to provide an inert gas-treated catalyst having less than about 10 wt % organic material disposed thereon;
 contacting the inert gas-treated catalyst with an oxygen-containing gas at a temperature of at least about 200° C., the contacting being performed to substantially remove any residual carbonaceous material remaining disposed on the dewaxed catalyst, thereby forming an oxidized catalyst;

contacting the oxidized catalyst with a hydrogen-containing gas at a temperature of at least about 200° C., the hydrogen-containing gas comprising at least 10 vol % hydrogen, thereby forming a regenerated catalyst; and disposing the regenerated catalyst in a second organic material;

wherein the oxygen concentration of the oxygen-containing gas increases throughout the contacting of the dewaxed catalyst with the oxygen-containing gas;

and wherein the contacting with increasing oxygen concentrations is performed such that the temperature of the catalyst remains below 400° C.

2. The process according to claim 1, wherein the first organic material has a congealing point in the range of about 60° C. to about 120° C., and the second organic material has a congealing point in the range of about 40° C. to about 125° C.

3. The process according to claim 1, wherein the catalytic metal is cobalt.

4. The process according to claim 1, wherein removing a substantial portion of the first organic material from the catalyst comprises contacting the catalyst disposed in the first organic material with a flow of a first gas at a temperature of at least about 70° C.

5. The process according to claim 1, wherein washing of the catalyst is not performed.

6. The process according to claim 1, wherein the contacting of the dewaxed catalyst with the flow of the substantially inert gas is performed to provide an inert gas-treated catalyst having less than about 5 wt % organic material disposed thereon.

7. The process according to claim 1, wherein the contacting of the dewaxed catalyst with the flow of the substantially inert gas is performed to provide an inert gas-treated catalyst having less than about 1 wt % organic material disposed thereon.

8. The process according to claim 1, wherein the substantially inert gas includes less than 5 vol % of hydrogen and less than 5 vol % of oxygen.

9. The process according to claim 8, wherein the substantially inert gas includes less than 1 vol % of hydrogen.

10. The process according to claim 8, wherein the substantially inert gas includes less than 0.1 vol % of oxygen.

11. The process according to claim 8, wherein the substantially inert gas includes less than 5 vol % of water.

12. The process according to claim 1, wherein the contacting with increasing oxygen concentrations is performed such that the temperature of the catalyst does not increase more than about 30° C. during the contacting with the oxygen-containing gas.

13. The process according to claim 1, wherein the increase in oxygen concentration is performed stepwise, and each step in oxygen concentration is performed such that the increase in catalyst temperature is no more than 3° C. per step.

14. The process according to claim 1, wherein the process further comprises, during the contacting with the oxygen-containing gas, measuring the temperature of the catalyst and using the result of the temperature measurement to determine the rate of increase of the oxygen concentration that maintains the temperature of the catalyst at 400° C. or less.

15. The process according to claim 1, wherein the oxidized catalyst has less than 1.0 wt % carbonaceous material disposed thereon.

16. The process according to claim 1, wherein at least about 40 mol % of the catalytic metal in the regenerated catalyst is in a zero-valent oxidation state.

17. The process according to claim 1, further comprising disposing the regenerated catalyst in a reactor.

18. The process according to claim 1, further comprising contacting the regenerated catalyst with carbon monoxide and hydrogen to form one or more hydrocarbons.

* * * * *